United States Patent [19]

Coates et al.

[11] Patent Number: 5,192,742

[45] Date of Patent: Mar. 9, 1993

US005192742A

[54] COMPOUNDS AND COMPOSITIONS FOR THE TREATMENT OF BACTERIAL INFECTIONS IN ANIMALS

[75] Inventors: Nigel J. Coates; Rachel Sykes; Davis Christopher J.; Lawrence M. Curtis, all of Betchworth, England

[73] Assignee: Beecham Group PLC, England

[21] Appl. No.: 809,845

[22] Filed: Dec. 18, 1991

Related U.S. Application Data

[63] Continuation of Ser. No. 454,708, Dec. 21, 1989, abandoned.

[30] Foreign Application Priority Data

Dec. 23, 1989 [GB] United Kingdom ............... 8830225

[51] Int. Cl.$^5$ .................... A61K 37/02; A61K 35/74; C07K 7/54; C07K 9/00
[52] U.S. Cl. ........................................ 514/8; 514/9; 530/312; 530/322; 424/115; 424/118; 435/71.3; 435/169; 435/170; 435/252.1; 435/253.2; 435/826; 435/872; 930/270; 930/DIG. 510
[58] Field of Search ............... 514/8, 9; 530/317, 322; 424/115, 118; 435/71.3, 169, 170, 252.1, 253.2, 826, 872

[56] References Cited

U.S. PATENT DOCUMENTS 4,920,215  4/1990  Holdom et al. .................... 424/116

FOREIGN PATENT DOCUMENTS 0211490  2/1987  European Pat. Off. .
0218099  4/1987  European Pat. Off. .

OTHER PUBLICATIONS

Lechevalier et al., International Journal of Systematic Bacteriology, vol. 36, No. 1, pp. 29–37 (1986).
Kirk-Othmer, Encyclopedia of Chemical Technology, (John Wiley and Sons, New York) third ed, vol. 2, p. 809 (1978).
Rudinger, Peptide Hormones, Parsons (Ed.), U Park Press, Baltimore, pp. 1–7 (1976).

Primary Examiner—Y. Christina Chan
Attorney, Agent, or Firm—Rosenman & Colin

[57] ABSTRACT

New glycopeptide antibiotics MM 49728, MM 55266, MM 55267/1, MM 55267/2 and MM 55268 are produced by fermentation of Amycolatopsis sp. NCIB 40089.

11 Claims, No Drawings

COMPOUNDS AND COMPOSITIONS FOR THE TREATMENT OF BACTERIAL INFECTIONS IN ANIMALS this is a continuation of application Ser. No. 454,708 filed Dec. 21, 1989, abandoned.

The present invention relates to novel antibacterially active materials obtainable from a microorganism, to processes for their production, and to their pharmaceutical use.

A large number of microorganisms have been isolated from nature and certain of those microorganisms have been found to produce various metabolites, which can be isolated and some of which have useful antibacterial activity. One such metabolite is a substance which has been designated MM 49728. It is believed to be a novel complex of glycopeptide compounds and it has been found to have useful antibacterial activity.

The present invention accordingly provides the novel substance MM 49728.

The substance MM 49728 has the following characteristics:

(i) it may be obtained by the cultivation of a microorganism of the genus Amycolatopsis;

(ii) the complex includes four substances which have been designated MM 55266, MM 55267/1, MM 55267/2, and MM 55268; and (iii) it shows antibacterial activity against *Staphylococcus aureus* V573.

The said MM 55266, MM 55267/1, MM 55267/2, and MM 55268 are believed to be novel substances, and each therefore forms a further aspect of the invention, together with its production and use. They have the characterizing data set out hereinbelow in the experimental section.

MM 55266 is believed to consist of a compound of formula (I):

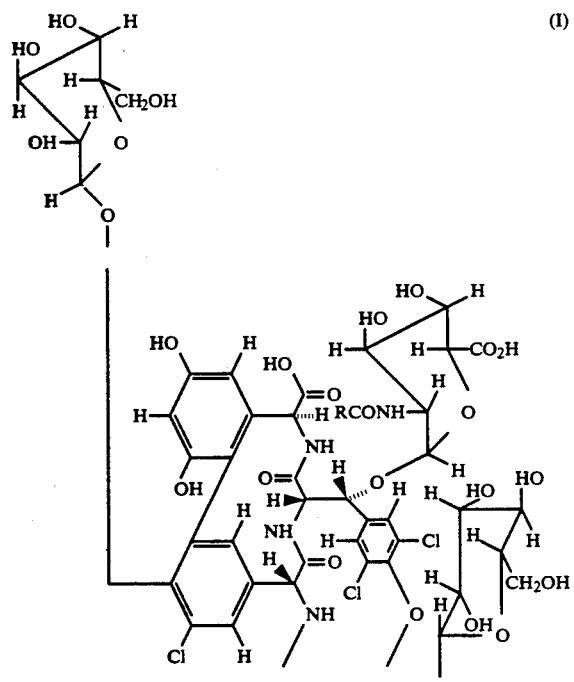

-continued

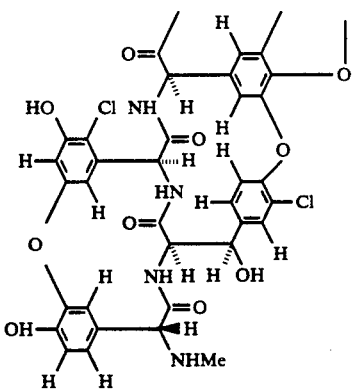

wherein R is $C_8H_{17}$ and can exist in more than one isomeric form.

A further aspect of the invention therefore provides a compound of formula (I), typically as a mixture of isomers.

Each of MM 55267/1, MM 55267/2 and MM 55268 is believed to consist of a glycopeptide compound which may exist as a mixture of isomers.

The present invention also provides a process for the production of a substance or compound of the invention which comprises cultivating a producing microorganism and subsequently isolating the substance or compound or a derivative thereof from the culture.

The present invention furthermore provides a process for the preparation of a substance or compound of the invention which comprises separating the substance or compound or a derivative thereof from a solution thereof in admixture with other antibacterially active substances and/or inactive substances by adsorption onto an affinity resin.

The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the cultivation process according to the invention include bacterial strains belonging to the genus Amycolatopsis that are capable of elaborating MM 49728. It has further been found that an example of such a strain is sp. NCIB 40089 and also mutants thereof, which has been isolated from nature.

The term 'mutant' as used herein includes any mutant strain which arises spontaneously or through the effect of an external agent whether that agent is applied deliberately or otherwise. Suitable methods of producing mutant strains including those outlined by H. I. Adler in 'Techniques for the Development of Microorganisms' in 'Radiation and Radioisotopes for Industrial Microorganisms', Proceedings of a Symposium, Vienna, 1973, page 241, International Atomic Energy Authority, and these include:

(i) Ionizing radiation (e.g. X-rays and λ-rays), u.v. light, u.v. light plus a photosensitizing agents (e.g. 8-methoxypsoralen), nitrous acid, hydroxylamine, pyrimidine base analogues (e.q. 5-bromouracil), acridines, alkylating agents (e.g. mustard gas, ethylmethane sulphonate), hydrogen peroxide, phenols, formaldehyde, heat, and (ii) Genetic techniques, including, for example, recombination, transformation, transduction, lysogenisation, lysogenic conversion, protoplast fusion and selective techniques for spontaneous mutants.

Sp. NCIB 40089 is believed to be a previously unreported species in the genus Amycolatopsis and therefore also forms a part of the present invention, particularly in biologically pure form. It has been deposited at the National Collections of Industrial and Marine Bacteria Ltd. (N.C.I.B), Aberdeen, Scotland under number 40089 on 6th December, 1988.

The fermentation medium for cultivating sp. NCIB 40089 suitably contains sources of assimilable carbon and assimilable nitrogen together with inorganic salts. Suitable sources of nitrogen include yeast extract, soyabean flour, meat extract, cottonseed, flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium), halogen ions (for example, chloride), and alkaline earth metal ions (for example calcium and magnesium), as well as trace elements such as iron and cobalt.

The cultivation may suitably be effected at a temperature of about 20° to 35° C., advantageously 20° to 30° C., and the culture may suitably be harvested up to 7 days, advantageously about 3 to 5 days, after the initiation of fermentation in order to give an optimum yield of the product.

The desired product or a derivative thereof may then be isolated from the culture medium and worked up and purified using conventional techniques for glycopeptide compounds. All such isolation and purification procedures may conveniently be effected at cool to ambient temperature, for example at a temperature within the range of from 4° to 30° C., conveniently from 20° to 25° C.

The desired product is generally obtained predominantly from the culture filtrate, and it is therefore convenient for the first isolation step to involve removal of solid material from the fermentation broth by, for example, filtration or centrifugation, to give a clarified culture filtrate.

Further isolation of the desired product from the clarified culture filtrate may conveniently be effected by adsorption onto an affinity resin such as D-alanyl-D-alanine-sepharose affinity resin.

The desired product may readily be identified in a routine manner by testing for antibacterial activity and/or by monitoring the HPLC retention time.

Suitably, the separation procedure may include a high-performance liquid chromatography step, preferably as the last step. Elution may be effected using aqueous $NaH_2PO_4$/acetonitrile.

The products according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a product according to the invention may, for example, be used in the preparation of a more pure form of the same product or of a related product (for example a corresponding derivative) suitable for pharmaceutical use.

The products of the invention have antibacterial properties and are useful for the treatment of bacterial infections in animals, especially mammals, including humans, in particular humans and domesticated animals (including farm animals). The products may be used for the treatment of infections caused by a wide range of organisms including, for example, those mentioned herein.

The present invention provides a pharmaceutical composition comprising a product of the invention or a pharmaceutically acceptable derivative thereof together with a pharmaceutically acceptable carrier or excipient.

The present invention also provides a method of treating bacterial infections in animals, especially in humans and in domesticated mammals, which comprises administering a product of the invention or a pharmaceutically acceptable derivative thereof, or a composition according to the invention, to a patient in need thereof.

The products according to the invention may be formulated for administration in any convenient way for use in human or veterinary medicine, by analogy with other antibiotics.

The products according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for exam-le, preservatives, solvents to assist drug penetration, and emollients in ointments and creams. Such typical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the active and a sterile vehicle, water being preferred. The active, depending on the vehicle and concentration used, may be either suspended or dissolved in the vehicle. In preparing solutions, the active may be dissolved in water for injection and filter-sterilised before being filled into a suitable vial or ampoule, which is then sealed. Advantageously, conventional additives including, for example, localanaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and an accompanying vial of water for injection may be supplied to reconstitute the liquid prior to use. Parenteral suspensions may be prepared in substantially the same manner except that the active is suspended in the vehicle instead of being dissolved and sterilisation cannot be accomplished by filtration. The active may instead be sterilised by exposure to ethylene oxide before being suspended in the sterile vehicle. Advantageously, a surfactant or wetting agent is included in such suspensions in order to facilitate uniform distribution of the active.

A product according to the invention may suitable be administered to the patient in an antibacterially effective amount.

A composition according to the invention may suitably contain from 0.1% by weight, preferably from 10 to 60% by weight, of a product according to the invention (based on the total weight of the composition), depending on the method of administration.

The products according to the invention may suitably be administered to the patient at a daily dosage of from 1.0 to 50 mg/kg of body weight. For an adult human (of approximately 70 kg body weight), from 50 to 3000 mg, for example about 1500 mg, of a product according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a product according to the invention.

The following Examples illustrate the preparation of products according to the present invention.

EXAMPLE 1

Production and Isolation of MM 49728 a) Fermentation

Culture NCIB 40089 was grown for 7 days at 26° C. on a solid agar slant in a MCCARTNEY bottle. The agar medium had the following composition:

| Constituent | Amount (g/l) |
| --- | --- |
| Yeast extract | 4.0 |
| Malt extract | 10.0 |
| Dextrose | 4.0 |
| Agar | 20.0 |
| Deionised water | To 1 liter |

[The constituents were all 'BACTO' products (Bacto is a Trade Mark) as supplied by Difco Laboratories, P.O. Box 14B, Central Avenue, East Molesey, Surrey]. The medium was adjusted to pH7.3 before sterilisation.

A spore suspension was prepared by adding 10 ml of sterilised water containing 0.02% Triton 80 to a MCCARTNEY bottle agar culture of NCIB 40089 and scraping the surface with a wire loop. Portions (2 ml) of spore suspension were used to inoculate the seed medium (100 ml) contained in 500 ml conical flasks closed with cotton gauze caps.

Fermentation was then carried out for 72 hrs at 28° C. and 240 rpm on a gyratory shaker.

15 liters of fermentation medium, together with 0.1% antifoaming agent, Polypropylene Glycol P2000, was sterilised in a 20 liter, fully baffled fermenter for 1 hour at 121° C. The fermenter was stirred by an agitator fitted with three, vaned-disc impellers at 200 rpm and supplied with sterile air at 0.5 volumes per volume per minute. 200 ml of vegetative inoculum from the seed stage were used to inoculate the fermenter and incubation was carried out at 28° C. for 4 days. An overpressure of air of 0.5 bar was maintained throughout. The fermentation was harvested after 4 days and clarified by centrifugation.

The seed and fermentation media were of the same composition. The medium contained:

| Constituent | Amount (g/l) |
| --- | --- |
| Soya bean flour | 10.0 |
| Glycerol | 20.0 |
| Maltose | 2.0 |
| $CoCl_2.6H_2O$ | 0.005 |
| Trace element solution | 10 ml |
| Deionised water | to 1 liter |

Trace element solution contained:

| Constituent | Amount (g/l) |
| --- | --- |
| $CaCl_2.2H_2O$ | 10.0 |
| $MgCl_2.6H_2O$ | 10.0 |
| NaCl | 10.0 |
| $FeCl_3$ | 3.0 |
| $ZnCl_2$ | 0.5 |
| $CuCl_2.2H_2O$ | 0.5 |
| $MnSO_4.4H_2O$ | 0.5 |

The medium was adjusted to pH 7.3 before sterilisation at 117° C. for 15 minutes.

(The soya bean flour was ARKASOY '50' supplied by Arkady - ADM, Manchester, UK).

b) Isolation of MM 49728

An aliquot of clarified broth (5 liters) prepared as described in a) was adjusted to pH 7.0 and applied to a (0.59 liter) DIAION HP20 column. (HP20 was supplied by Mitsubishi Chemical Industries, Tokyo, Japan). The column was washed with deionised water (1 liter) and then eluted with 50% Propan-1-ol in 0.1M ammonia. 16 ml fractions were collected. Those fractions with antibacterial activity (23–40) were bulked and concentrated in vacuo. 0.05M $NaH_2PO_4$ was added to the concentrated solution to give a total of 1 liter. This solution was then applied to a (1 liter) CM SEPHADEX C25 cation exchange column ($Na^+$ form) previously equilibrated with 0.05M $NaH_2PO_4$ pH 6.5. (CM SEPHADEX was supplied by Pharmacia Ltd., Uppsala, Sweden). The column was washed with 0.05M $NaH_2PO_4$ pH 7.0 (1 liter) and then eluted using an exponential gradient of 0.05M $NaH_2PO_4$ pH 7.0 to 0.2M $Na_2HPO_4$ pH 9.5 (500 ml in mixing vessel). 20 ml fractions were collected. Antibacterial activity was detected in fractions 2–40 which were bulked (0.75 liter).

Inorganic impurities were removed from this bulk by stirring for 1 hour with D-alanyl-D-alanine sepharose affinity resin at pH 7.0. The affinity adsorbent was prepared from D-alanyl-D-alanine immobilised on activated CM SEPHAROSE 4B (6-aminohexanoic acid-activated-sepharose 4B was obtained from Sigma Chemical Co., Poole, Dorset). The mixture was filtered onto a glass scinter funnel and the filtrate discarded. The affinity resin was resuspended in deionised water (1 liter) and filtered as before. The resin was washed twice more with deionised water (2×800 ml) and then eluted with 0.1M ammonia containing 50% acetonitrile (4×200 ml aliquots). The eluate fractions were evaporated under reduced pressure and those containing antibacterial activity were freeze-dried to yield 103 mg of MM 49728.

MM 49728 was monitored by high performance liquid chromatography using a 3.9 mm ×300 mm WATERS uBONDAPAK $C_{18}$ reverse phase column, eluting with 0.1M $NaH_2PO_4$ pH 6.0 containing 25% acetonitrile at a flow rate of 2 ml/min. The eluate was monitored for UV absorbance at 220 nm. Under these conditions MM 49728 had a retention time of 18.1 mins.

Properties of MM 49728

FAB mass spectroscopy indicated the presence of two ions corresponding to molecular weights of 1968±2 and 1982±2.

The antibacterial activity of material produced essentially as in example 1 was determined by the microtitre method. OXOID No. 2 broth (supplied by Oxoid Ltd., Wade Road, Basingstoke, Hampshire, UK., (OXOID is a trade mark)) was used for all organisms except for the Streptococcus spp. which was tested using TODD HEWITT broth 'supplied by Oxoid Ltd.). Inoculum were overnight broth cultures diluted ten-fold. The microtitre plates were incubated for 24 hours at 37° C. The results are shown in Table 1.

TABLE 1

Antibacterial activity of MM 49728 against a range of organisms determined by the microtitre method (MIC μg/ml)

| Organism | MM 49728 |
|---|---|
| Bacillus subtilis ATCC 6633 | 2.0 |
| Corynebacterium xerosis NCTC 9755 | ≦0.5 |
| Sarcina lutea NCTC 8340 | 4.0 |
| Staphylococcus aureus | |
| Smith | 8.0 |
| Oxford | 2.0 |
| Russel | 4.0 |
| V573 MR* | 1.0 |
| S. saprophyticus | |

TABLE 1-continued

Antibacterial activity of MM 49728 against a range of organisms determined by the microtitre method (MIC μg/ml)

| Organism | MM 49728 |
|---|---|
| FL1 | 16.0 |
| FL2 | 8.0 |
| S. epidermidis | |
| 60137 | 2.0 |
| 54815 | 4.0 |
| Streptococcus pyrogenes | |
| CN10 | ≦0.5 |
| 1950 | ≦0.5 |
| S. agalactiae 'Hester' | ≦0.5 |
| S. sanguis ATCC 10556 | 1.0 |
| S. viridans 'Harding' | 1.0 |
| S. pneumoniae Pu7 | 1.0 |
| S. faecalis I | 1.0 |

*Multi-resistant (Methicillin, Tetracycline, Erythromycin and Gentamicin resistant).

Preparation of affinity absorbent

The N-hydroxysuccinimide ester of 6-aminohexanoic acid SEPHAROSE 4B (60 g) was placed on a glass scinter and washed with 1 mM hydrochloric acid solution (2L) under suction. The wet cake was then added to a solution of D-alanyl-D-alanine (1.5 g) in 0.1M sodium bicarbonate solution (60 ml) and occasionally shaken over the next hour. The suspension was filtered under suction and the residue suspended in 0.1M tris(-hydroxymethyl)amino methane (TRIS) (100 ml) for 1 hour and then refiltered through a glass sinter. The cake was washed successively with 0.1M sodium bicarbonate solution, 0.05M TRIS (containing 0.5M sodium chloride), 0.05M formate buffer at pH 4.0 (containing 0.5M sodium chloride) and finally distilled water. The affinity resin was then stored at 4° C. in aqueous suspension.

EXAMPLE 2 a) Fermentation

All seed and production stages used the liquid medium as described in Example 1a. A 1 ml vegetative cell suspension of culture NC1B 40089 stored in 20% glycerol and 10% lactose under liquid nitrogen, was used to inoculate 100 ml of fermentation medium contained in a 500 ml conical flask, stoppered with a foam plastic bung. After incubation for 72 hours at a temperature of 28° C. and 240 rpm on a gyratory shaker, 4 ml aliquots were transferred to 500 ml conical flasks containing 100 ml fresh medium. These were incubated at 28° C. and 240 rpm for a further 48 hours.

15 liters of fermentation medium together with 0.1% antifoaming agent, polypropylene glycol P2000, was sterilised in situ for 60 minutes at 121° C. in a 20 liter, fully baffled fermenter. The fermenter was stirred by a bottom driven agitator fitted with three vaned-disc impellers at 200 rpm during both sterilization and cultivation. 400 ml vegetative inoculum from the second stage seed flasks was used to inoculate the fermenter and incubation was carried out at 280° C. for 45 hours before transfer to the production stage. During the fermentation the fermenter was supplied with sterile filtered air at 0.23 volumes per volume per minute and an overpressure of air of 0.5 bar was maintained throughout.

The fermenter was harvested in 50L portions which were adjusted to pH 10.9 by addition of 5M Na OH, prior to centrifugation. The resulting supernatant was adjusted to pH 6-8 by addition of 5M H Cl.

b) Isolation of glycopeptide complex

The neutralised clarified broth (270l) was applied to a 22L column of DIAION HP20 at a flow rate of 1L min$^{-1}$. The column was washed with 30L of deionised water and the percolate and water wash discarded. The active material was eluted from the column with 0.1M ammonia containing 50% propan-2-ol. 1 liter fractions were collected. Fractions with antibiotic activity, (16-35), were bulked and evaporated in vacuo to 8.8 L.

8.8 L of aqueous concentrate was mixed with 4.5 L of butan-1-ol and the pH adjusted to 3.0 by the addition of 0.1M hydrochloric acid. Phases were separated under gravity and the lower aqueous phase removed. The upper solvent phase and mixed phases were separated by centrifugation and the solvent phase recovered by aspiration. 4.5L of solvent phase was mixed with an equal volume of deionised water and the pH was adjusted to 10.0 by addition of 0.1M sodium hydroxide. Phases were separated under gravity and 4.7L of aqueous phase adjusted to pH 7.0 with 0.1M hydrochloric acid. The aqueous phase was concentrated in vacuo until a gelatinous precipitate was formed, which was removed by filtration. The precipitate was resuspended in deionised water and refiltered via 541 filter papers [Filters supplied by Whatman, Springfield Mill, Maidstone, Kent, England.]

The combined filtrates (6.3L) were stirred for 1 hour with D-alanyl-D-alanine-sepharose affinity resin, (350 ml wet volume). [Prepared as described in example 1]. The mixture was treated as previously described to give the combined eluates which were evaporated in vacuo to give 2.3L of aqueous concentrate.

The 7.45L of affinity percolate was retreated with 350 ml of affinity adsorbent as above to give a further 2.55L of aqueous concentrate.

4.85L of combined concentrates were freeze dried to yield 15.2 g of glycopeptide complex, MM 49728 which contained a mixture of MM 55266, MM 55267 and MM 55268.

EXAMPLE 3

Isolation of MM 55266

2 g of MM 49728, prepared as described in example 2b was dissolved in 400 ml of 5% methanol in water at pH 8.0. This solution was applied to a 270 ml column of MATREX C$_{18}$ reverse phase silica, (30 μm particles, 60A pore diameter), previously equilibrated in 0.1M NaH$_2$PO$_4$, pH 6.0. (Matrex supplied by Amicon, Upper Mill, Stonehouse, Gloucestershire, England).

The column was washed with 50 ml of the equilibrating buffer before being eluted at 15 ml. min$^{-1}$ with the above buffer, containing 15% acetonitrile (500 ml) and 20% acetonitrile (500 ml). These percolates, washes and eluates were discarded. The elution continued with the buffer containing 25% acetonitrile and the eluate was collected in 20 ml fractions.

The fractions were monitored by HPLC using a 3.9×150 mm WATERS NOVAPAK C$_{18}$ reverse phase column, eluting with 0.1M Na H$_2$ PO$_4$ pH 6.0, containing 25% acetonitrile at a flow rate of 2 ml.min$^{-1}$. The eluate was monitored for UV absorbance at 220 nm. Under these conditions, MM 55266 had a retention time of 4.4 minutes.

Fractions containing mainly MM 55266, (29-40), were bulked, evaporated in vacuo to 160 ml and applied to a 60 ml column of DIAION HP20 at a flow rate of 4 ml.min$^{-1}$. The column was washed with 140 ml of deionised water and the percolate and water wash discarded. The column was eluted with 240 ml of 50% methanol and the eluate evaporated in vacuo to 108 ml.

The aqueous concentrate was adjusted to pH 6.5 by addition of Na H$_2$ PO$_4$ and applied to a DYNAMAX 150-A preparative HPLC column, 10×300 mm, containing 12 μm particles of C$_{18}$ reverse phase silica previously equilibrated in 0.05M NaH$_2$PO$_4$ pH 6.0. [Column supplied by Rainin Instrument Co, Woburn, Mass., USA].

The column was washed with 20 ml of the equilibrating buffer and eluted with the buffer containing a programmed gradient of acetonitrile at 5 ml.min$^{-1}$. The eluate was collected in 5 ml fractions. From 2-12 minutes, the acetonitrile content was increased linearly to 23% where it was held constant for 20 minutes. From 32-112 minutes, the acetonitrile content was increased to 27%.

The fractions were monitored by HPLC on a WATERS NOVPAK column as previously described. Fractions containing MM 55266, (84-96), were bulked and evaporated in vacuo to 45 ml.

The aqueous concentrate was stirred for 1 hour with D-alanyl-D-alanine-sepharose affinity resin, (8 ml wet volume). [Prepared as described in example 1]. The mixture was treated as previously described and the combined eluates were evaporated in vacuo and freeze dried to yield 130 mg of MM 55266.

FAB mass spectroscopy indicated a molecular ion corresponding to a molecular weight of 1968±1.

EXAMPLE 4

Isolation of MM 55267 complex

The preparative HPLC separation described in example 3 also yielded fractions containing MM 55267 (68-75) which were bulked and evaporated in vacuo to 25 ml.

MM 55267 was monitored by HPLC on a WATERS NOVAPAK column as previously described. Under these conditions, MM 55267 had a retention time of 4.0 minutes.

The aqueous concentrate was stirred for 1 hour with D-alanyl-D-alanine-sepharose affinity resin, (2 ml wet volume). [Prepared as described in example 1]. The mixture was treated as previously described and the combined eluates were evaporated in vacuo and freeze dried to yield 25 mg of MM 55267. FAB mass spectroscopy indicated the presence of two molecular ions corresponding to molecular weights of 2190±1 and 2204±1, designated MM 55267/1 and MM 55267/2, respectively.

EXAMPLE 5

Isolation of MM 55268

2 g of MM 49728, prepared as described in example 2b, were dissolved in 200 ml of water at pH8.0 and filtered via 542 filter papers. [Filters supplied by Whatman, Springfield Mill, Maidstone, Kent, England.]The solids obtained were resuspended in water and refiltered to give a combined filtrate of 500 ml.

This solution was applied to a 270 ml column of MATREX C$_{18}$ reverse phase silica, (30 μm particles, 60A pore diameter) previously equilibrated in 0.05 M NaH$_2$PO$_4$, pH 6.0.

The column was washed with 200 ml of the equilibrating buffer before being eluted at 16 ml.min$^{-1}$ with the buffer, containing 20% acetonitrile (300 ml). These percolates, washes and eluates were discarded. The elution continued with the buffer containing 25% acetonitrile and the eluate was collected in 16 ml fractions.

The fractions were monitored by HPLC on a WATERS NOVAPAK column as previously described. Under these conditions, MM 55268 had a retention time of 9.2 minutes.

Fractions containing MM 55268, (85-120), were bulked, evaporated in vacuo to 160 ml and applied to a 60 ml column of DIAION HP20 at a flow rate of 4 ml.min.$^{-1}$. The column was washed with 200 ml of deionised water and the percolate and water wash discarded. The column was then eluted with 200 ml of 50% methanol in water which was discarded and finally by 250 ml of methanol. The methanol eluate was mixed with 200 ml of deionised water and evaporated in vacuo to 155 ml. The resulting white precipitate was filtered off and dissolved in deionised water. The combined solutions were then filtered through GF/F glass fibre filters. [Filters supplied by Whatman] and freeze dried to yield 488 mg of MM 55268.

FAB mass spectroscopy indicated a molecular ion corresponding to a molecular weight of 1982±1.

Detection Methods.

a) Fermentation samples and column fractions were monitored for antibiotic activity by bioassay on Staphylococcus aureus V573, using the conventional hole in plate method.

b) MM 55266, MM 55267 and MM 55268 have a characteristic UV maximum at 280 nm. Purified samples can be assayed using direct measurement of this absorbance.

The antibacterial activities of MM 55266, MM 55267 and MM 55268 were determined by the microtitre method as described in Example 1b.

The results are shown in tables 2, 3 and 4.

TABLE 2

Antibacterial activity of MM 55266 against a range of organisms, determined by the microtitre method.
(MIC µg/ml)

| Organism | MM 55266 |
|---|---|
| Bacillus subtilis ATCC 6633 | 4.0 |
| Corynebacterium xerosis NCTC 9755 | 8.0 |
| Sarcina lutea NCTC 8340 | 4.0 |
| Staphylococcus aureus | |
| 'Oxford' | 4.0 |
| 'Russell' | 8.0 |
| 'V573' MR* | 2.0 |
| S. saprophyticus 'FLI' | 16.0 |
| S. epidermidis 60137 | 8.0 |
| Streptococcus pyrogenes CN10 | 2.0 |
| Streptococcus agalaetiae 'Hester' | 4.0 |
| Streptococcus sanguis ATCC 10556 | 4.0 |
| Streptococcus pneumoniae Pu7 | 2.0 |
| Streptococcus faecalis 1 | 8.0 |

*Multi-resistant (Methicillin, tetracycline, erythromycin and gentamycin resistant.)

TABLE 3

Antibacterial activity of MM 55267 against a range of organisms, determined by the microtitre method.
(MIC µg/ml)

| Organism | MM 55267 |
|---|---|
| Bacillus subtilis ATCC 6633 | 16.0 |
| Corynebacterium xerosis NCTC 9755 | 16.0 |
| Sarcina lutea NCTC 8340 | 16.0 |
| Staphylococcus aureus | |
| 'Oxford' | 32.0 |
| 'Russell' | 64.0 |
| 'V573' MR* | 16.0 |
| S. saprophyticus 'FLI' | 64.0 |
| S. epidermidis 60137 | 16.0 |
| Streptococcus pyrogenes CN10 | 4.0 |
| Streptococcus agalaetiae 'Hester' | 8.0 |
| Streptococcus sanguis ATCC 10556 | 16.0 |
| Streptococcus pneumoniae Pu7 | 8.0 |
| Streptococcus faecalis 1 | 32.0 |

*Multi-resistant (Methicillin, tetracycline, erythromycin and gentamycin resistant)

TABLE 4

Antibacterial activity of MM 55268 against a range of organisms, determined by the microtitre method.
(MIC µg/ml)

| Organism | MM 55267 |
|---|---|
| Bacillus subtilis ATCC 6633 | 4.0 |
| Corynebacterium xerosis NCTC 9755 | 4.0 |
| Sarcina lutea NCTC 8340 | 2.0 |
| Staphylococcus aureus | |
| 'Oxford' | 4.0 |
| 'Russell' | 4.0 |
| 'V573' MR* | 1.0 |
| S. saprophyticus 'FLI' | 8.0 |
| S. epidermidis 60137 | 4.0 |
| Streptococcus pyrogenes CN10 | 0.25 |
| Streptococcus agalaetiae 'Hester' | 2.0 |
| Streptococcus sanguis ATCC 10556 | 2.0 |
| Streptococcus pneumoniae Pu7 | 1.0 |
| Streptococcus faecalis 1 | 4.0 |

*Multi-resistant (Methicillin, tetracycline, erythromycin and gentamycin resistant)

Characterising data

Physical and spectroscopic properties of MM 55266.
FAB-MS (glycerol/thioglycerol/acetic acid) MH+1969±1

Molecular Weight : 1968

Molecular Formula : $C_{86}H_{89}N_8O_{35}Cl_5$

UV($H_2O$) λ max 280 nm (ε8680)

$^1$H NMR in DMSO $d_6$ at 353° K. Tetramethylsilane as internal standard.

δH 8.60 (1H, d, J 6 Hz), 8.12 (1H, d, J 6.4 Hz), 7.80 (1H, s), 7.72 (1H, d, J 9.4 Hz), 7.50 (1H, br.d), 7.46 (1H, d, J 10.6 Hz), 7.38 (1H, d, J 2 Hz), 7.35 (1H, d, J 7.5 Hz), 7.28 (1H, d, J 8.5 Hz), 7.25 (1H, d, J 2 Hz), 7.20 (1H, d, J 8.2 Hz), 7.13 (1H,s),7.09 (1H, d, J 9.9 Hz), 6.82 (1H, d, J 2.1 Hz), 6.78 (1H, d, J 1 Hz), 6.59 (2H, overlapping m), 6.41 (1H, d, J 2.0 Hz), 6.37 (1H, d, J 2 Hz), 6.1 (1H, br.d), 6.07 (1H, d, J 10.6 Hz), 5.81 (1H, s), 5.69 (1H, d, J 7.3 Hz), 5.39 (1H, d, J 7.5 Hz), 5.33 (1H, s), 5.26 (1H, d, J 1.4 Hz), 5.15 (1H, d, J 5.1 Hz), 5.11 (1H, s), 5.08 (1H, m), 4.53 (1H, d, J 6.2 Hz), 4.41 (2H, overlapping d), 4.33 (1H, s), 4.12 (1H, d, J 11.1 Hz), 3.92 (1H, m), 3.7-3.0 (overlapping signals), 2.38 (3H, s), 2.17 (2H, m), 1.50 (2H, m), 1.25 ($CH_2$ envelope), 0.85 (6H, d, J 6.6 Hz)ppm.

HPLC: as above

Physical and spectroscopic properties of MM 55267
FAB-MS (glycerol/thioglycerol/acetic acid)
MH+2191±1 and 2205±1
Molecular weights : 2190 and 2204
HPLC: as above
Physical and spectroscopic properties of MM 55268
FAB-MS (dithiothreitol/dithioerythritol)
MNa+2005±1 ;MNa$_2$+2028±1
Molecular weight : 1982
HPLC: as above
We claim:

1. A compound of formula (I):

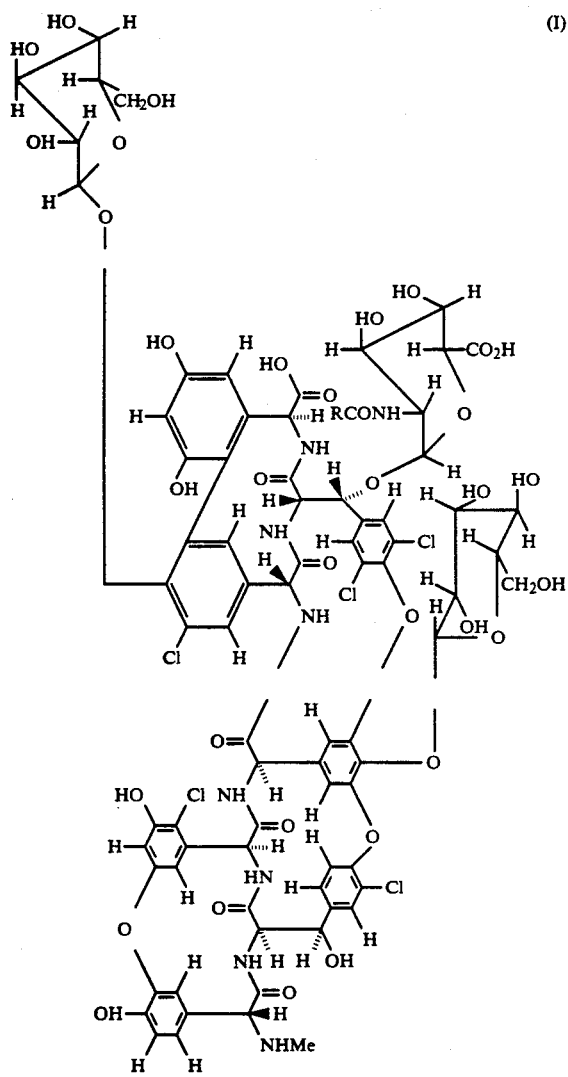

wherein R is $C_8H_{17}$, having the following NMR analysis: $^1H$ nmR in DMSO $d_6$ at 353°K; Tetramethylsilane as internal standard;

δH 8.60 (1H, d, J 6 Hz), 8.12 (1H, d, J 6.4 Hz), 7.80 (1H, s), 7.72 (1H, d, J 9.4 Hz), 7.50 (1H, br.d), 7.46 (1H, d, J 10.6 Hz), 7.38 (1H, d, J 2 Hz), 7.35 (1H, d, J 7.5 Hz), 7.28 (1H, d, J 8.5 Hz), 7.25 (1H, d, J 2 Hz), 7.20 (1H, d, J 8.2 Hz), 7.13 (1H,s),7.09 (1H, d, J 9.9 Hz), 6.82 (1H, d, J 2.1 Hz), 6.78 (1H, d, J 1 Hz), 6.59 (2H, overlapping m), 6.41 (1H, d, J 2.0 Hz), 6.37 (1H, d, J 2 Hz), 6.1 (1H, br.d), 6.07 (1H, d, J 10.6 Hz), 5.81 (1H, s), 5.69 (1H, d, J 7.3 Hz), 5.39 (1H, d, J 7.5 Hz), 5.33 (1H, s), 5.26 (1H, d, J 1.4 Hz), 5.15 (1H, d, J 5.1 Hz), 5.11 (1H, s), 5.08 (1H, m), 4.53 (1H, d, J 6.2 Hz), 4.41 (2H, overlapping d), 4.33 (1H, s), 4.12 (1H, d, J 11.1 Hz), 3.92 (1H, m), 3.7-3.0 (overlapping signals), 2.38 (3H, s), 2.17 (2H, m), 1.50 (2H, m), 1.25 ($CH_2$ envelope), 0.85 (6H, d, J 6.6 Hz)ppm.

2. A substance or compound obtained by fermentation of a microorganism of the genus Amycolatopsis NCIB 40089 accession number comprised of compounds having a molecular weight of 2190±1 and 2204±1 and having antibiotic activity measured in MIC μg/ml against *Bacillus subtilis* ATCC 6633 of 16.0, *Corynebacterium xerosis* NCTC 9755 of 16.0, *Sarcina lutea* NCTC 8340 of 16.0, *Staphylococcus aureus* "Oxford" of 32.0, *Staphylococcus aureus* "Russell" of 64.0, *Staphylococcus aureus* "V573" MR of 16.0, *Staphylococcus saprophyticus* "FLI" of 64.0, *Staphylococcus epidermidis* 60137 of 16.0, *Streptococcus pyogenes* CN10 of 4.0, *Streptococcus agalactiae* "Hester" of 8.0, *Streptococcus sanguis* ATCC 10556 of 16.0, *Streptococcus pneumoniae* Pu7 of 8.0 and *Streptococcus faecalis* 1 of 32.0, wherein said *Staphylococcus aureus* "V573" MR is resistant to methicillin, tetracycline, erythromycin and gentamycin.

3. A substance or compound obtained by fermentation of a microorganism of the genus Amycolatopsis NCIB 40089 accession number comprised of compounds having a molecular weight of 1982±1 and having antibiotic activity measured in MIC μg/ml against *Bacillus subtilis* ATCC 6633 of 4.0, *Corynebacterium xerosis* NCTC 9755 of 4.0, *Sarcina lutea* NCTC 8340 of 2.0, *Staphylococcus aureus* "Oxford" of 4.0, *Staphylococcus aureus* "Russell" of 4.0, *Staphylococcus aureus* "V573" MR of 1.0, *Staphylococcus saprophyticus* "FLI" of 8.0, *Staphylococcus epidermidis* 60137 of 4.0, *Streptococcus pyogenes* CN10 of 0.25, *Streptococcus agalactiae* "Hester" of 2.0, *Streptococcus sanguis* ATCC 10556 of 2.0, *Streptococcus pneumoniae* Pu7 of 1.0 and *Streptococcus faecalis* 1 of 4.0, wherein said *Staphylococcus aureus* "V573" MR is resistant to methicillin, tetracycline, erythromycin and gentamycin.

4. A substance or compound according to claim 2, in substantially pure form.

5. The substance or compound according to claim 2, comprising a compound of a molecular weight of 2190±1.

6. The substance or compound according to claim 2, comprising a compound of a molecular weight of 2204±1.

7. The substance or compound according to claim 5, in substantially pure form.

8. The substance or compound according to claim 6, in substantially pure form.

9. The substance or compound according to claim 3, in substantially pure form.

10. A pharmaceutical composition for the treatment of bacterial infection in animals, comprising an antibacterially effective amount of a substance or compound according to claim 2, together with a pharmaceutically acceptable carrier or excipient.

11. A method of treating bacterial infections in animals, which comprises administering an antibacterially effective amount of a substance or compound according to claim 2 to an animal in need thereof.

* * * * *